United States Patent [19]

Rosenkrans, Jr. et al.

[11] Patent Number: 5,096,822
[45] Date of Patent: Mar. 17, 1992

[54] BOVINE EMBRYO MEDIUM

[75] Inventors: Charles F. Rosenkrans, Jr., 111 Ridge Dr., Mt. Horeb, Wis. 53572; Carol L. Keefer, Madison, Wis.; Michelle M. Sims, 2204 Beatrice Ct., Stoughton, Wis. 53589

[73] Assignees: W. R. Grace & Co.- Conn., New York, N.Y.; Charles F. Rosenkrans, Jr., Mt. Horeb; Michelle M. Sims, Stoughton, both of Wis.

[21] Appl. No.: 558,969

[22] Filed: Jul. 26, 1990

[51] Int. Cl.$^5$ .......................... C12N 5/00; C12N 5/02
[52] U.S. Cl. .............. 435/240.1; 435/240.2; 435/240.25; 435/240.3
[58] Field of Search ............... 435/172.2, 172.3, 240.1, 435/240.26; 800/2, DIG. 6

[56] References Cited

U.S. PATENT DOCUMENTS

| 4,994,384 | 2/1991 | Prather et al. | 435/172.2 |
| 5,057,420 | 10/1991 | Massey | 435/172.2 |

OTHER PUBLICATIONS

Gordon, I. and K. H. Ku, 1990, "Production of Embryos In Vitro and its Impact on Livestock Production," *Theriogenology*, vol. 33, No. 1, pp. 77-87.

Bondioli, K. R. et al., 1990, "Production of Identical Bovine Offspring by Nuclear Transfer," *Theriogenology*, vol. 33, No. 1, pp. 165-174.

Marek, D. E. et al., 1990, "Nuclear Transplantation in the Bovine: Effect of Donor Embryo Age on Subsequent Embryo Production," *Theriogenology*, vol. 33, No. 1, p. 283.

Thibault, "La Culture In Vitro de L'Oeuf de Vache", *Annls. Biochim. Biophys.*, vol. 6, pp. 159-164 (1966).

Camous, et al., "Cleavage Beyond the Block Stage and Survival After Transfer of Early Bovine Embryos Cultured with Trophoblastic Vesicles", *J. Reprod. Fert.*, vol. 72, pp. 479-485 (1984).

Eyestone, et al., "Culture of One-and Two-Cell Bovine Embryos to the Blastocyst Stage in the Ovine Oviduct", *Theriogenology*, vol. 28, pp. 1-7 (1987).

Kane, M. T. and B. D. Bavister (1988, "Vitamin Requirements for Development of Eight-Cell Hamster Embryos to Hatching Blastocycsts In Vitro," *Biol. Reprod.*, 39, 1137-1143).

Zhang, X. and D. T. Armstrong (1990, "Presence of Amino Acids and Insulin in a Chemically Defined Medium Improves Development of 8-Cell Rat Embryos In Vitro and Subsequent Implantation In Vivo", *Biol. Reprod.*, 42, 662-668).

Sirard et al. (1988, *Biol. Reprod.*, 39, 546-552).

Parrish, J. J. et al., (1988, "Capacitation of Bovine Sperm by Heparin," *Biol. Reprod.* 38, 1171-1180).

Leibfried, M. L. and B. D. Bavister, 1982, "Effect of Epinephrine and Hypotaurine on in vitro Fertilization in the Golden Hamster," *J. Reprod. Fertil.*, 66, 87-93.

Seshagiri, P. B. and B. D. Bavister, 1989, "Glucose Inhibits Development of Hamster 8-cell Embryos In Vitro," *Biol. Reprod.*, 40, 599-606.

Prather, R. S. et al., 1987, "Nuclear Transfer in the Bovine Embryo: Assessment of the Donor Nuclei and Recipient Cytoplasm," *Biol. Reprod.*, 37, 859-866.

*Primary Examiner*—David L. Lacey
*Assistant Examiner*—Gian Wang
*Attorney, Agent, or Firm*—Andrus, Sceales, Starke & Sawall

[57] ABSTRACT

The present invention is directed to a bovine embryo culture medium. The medium includes a culture solution containing the nutritional substances necessary to support a bovine embryo. One of the nutritional substances is hemicalcium lactate in an amount effective to maintain the health and viability of the bovine embryo. The culture medium is a preferred nuclear transfer medium.

12 Claims, 7 Drawing Sheets

BOVINE EMBRYO MEDIUM

FIELD OF THE INVENTION

The present invention is generally directed to a bovine embryo medium and to a method for culturing bovine embryos in an in vitro culture medium. The present invention is specifically directed to a bovine embryo medium which will support bovine blastocyst development in vitro for normal and nuclear transferred embryos.

DESCRIPTION OF THE PRIOR ART

The fertilized egg or embryo, containing the male and female pronuclei, undergoes syngamy, i.e., the union of the male and female pronuclei to form a zygote nucleus, followed by a series of cell divisions. As the embryo undergoes a series of mitotic divisions, it develops through the morula stage to the blastocyst stage where tissue differentiation and specialization occur. Ultimately, this leads to the formation of the fetus and placenta, which become implanted in the uterus.

Preserving embryos in an embryo culture medium is an important feature in the animal industry today. At present, the embryo transfer industry is dependent on non-surgical removal of its small harvest of embryos from the uterus of a superovulated cow. Technologies to increase the supply of embryos by cloning and their genetic alteration by gene transfer are nearing commercial use. These technologies require production of embryos in vitro from in vitro matured and fertilized oocytes obtained from commercially slaughtered cattle as well as the ability to culture the embryos in vitro from fertilization to a stage compatible with transfer into the uterus of a recipient cow, commonly in the morula or blastocyst stage. Until now, the common system for developing bovine embryos from fertilization to morula or blastocyst, or from nuclear transfer to morula or blastocyst, has been culture for approximately five days in the oviduct of a sheep. Reference is made to the following citations for a description of current practices in this technology: Gordon, I. and K. H. Ku, 1990, "Production of Embryos In Vitro and its Impact on Livestock Production," *Theriogenology*, Vol. 33, No. 1, Pgs. 77–87; Bondioli, K. R. et al., 1990, "Production of Identical Bovine Offspring by Nuclear Transfer," *Theriogenology*, Vol. 33, No. 1, Pgs. 165–174; Marek, D. E. et al., 1990, "Nuclear Transplantation in the Bovine: Effect of Donor Embryo Age on Subsequent Embryo Production," *Theriogenology, Vol.* 33, No. 1, Pg. 283.

This surrogate oviduct system has allowed development of bovine embryos through a developmental block which previously has occurred prior to the blastocyst stage and at the 8- to 16-cell transition. While this procedure is effective, it is cumbersome and expensive. In addition, it requires the surgical exposure and ligation of the oviduct of the animal and often sacrifice of the animal. Once the embryo has matured to the blastocyst stage, it is then recovered for the genetic manipulation, cloning, or whatever manipulation is intended for it, after which it is placed back into the reproductive tract of a recipient (surrogate dam).

For successful commercial use of techniques such as genetic engineering or cloning, it must be possible to mature a single-cell embryo in vitro to the morula or blastocyst stage before it can be non-surgically transferred into a surrogate recipient dam to produce a pregnancy. However, bovine embryos encounter a block to in vitro bovine embryonic development at the 8- to 16-cell stage. Thibault, "La Culture In Vitro de' L'Oeuf de Vache", *Annls. Biochim. Biophys.*, Vol. 6, pp. 159–164 (1966), Camous, et al., "Cleavage Beyond the Block Stage and Survival After Transfer of Early Bovine Embryos Cultured with Trophoblastic Vesicles", *J. Reprod. Fert.*, Vol. 72, pp. 479–485 (1984). Numerous efforts have been made to overcome this block to in vitro embryo development.

Eyestone, et al., "Culture of One- and Two-Cell Bovine Embryos to the Blastocyst Stage in the Ovine Oviduct", *Theriogenology, Vol.* 28, pp. 1–7 (1987), reported that ligated ovine oviducts would support development of bovine embryos from the t-cell to blastocyst stage. Pregnancies and live calves were produced after transfer of cultured embryos to recipient heifers. Cultures of 1- and 2-cell embryos in the oviducts of intact cycling, ovariectomized and anestrous ewes produced morphologically normal morulae and blastocysts followed by pregnancies in recipient heifers, suggesting that ovarian activity was not required for normal embryo development in the oviduct.

These results suggest that there is a stage in bovine embryonic development, perhaps the 5- to 8-cell stage, which is a period of particular sensitivity to in vitro conditions, Therefore, it is likely that an important, environmentally sensitive event occurs around the 8-cell stage of embryonic development. Exposure of embryos to suboptimal conditions during this period may prevent the normal occurrence of this event, thus blocking further development.

It has been a goal of researchers to find a reliable in vitro culture system which will allow development of early bovine embryos to blastocyst stage. Such a development would effectively replace the surrogate oviduct system by an in vitro culture system and world greatly facilitate embryo manipulation procedures. The lack of a reliable in vitro culture system for early bovine embryos has hampered studies of early development and the application of these manipulations procedures.

There are a variety of culture media routinely used for the collection of embryos, and specifically bovine embryos. Examples of known culture media, which may be used for bovine embryo culture, include Ham's F- 10+10% fetal calf serum, Tissue Culture Medium-199 (TCM 199)+10% fetal calf serum, Tyrodes's-Albumin-Lactate-Pyruvate, Dulbecco's Phosphate Buffered Saline, Eagle's and Whitten's media. One of the most common culture media for the collection and freezing of embryos is Dulbecco's Phosphate Buffered Saline (PBS) incorporating 1 to 20% fetal calf serum, new born serum or steer serum. If the embryos are to be kept in an embryo culture medium for a substantial period of time, the PBS is normally supplemented with 10 to 20% serum.

The practices to date have generally incorporated a substantial amount of a protein into the medium in vitro to be used as a surfactant. The surfactant lowers the surface tension of embryo cell walls so the embryo cells will not stick to each other, to the sides of the containers, or to the surface of the solution, causing distress on the cells. Useful and commonly used animal proteins include fetal calf serum and bovine serum albumin (BSA). Fetal calf serum is generally included in amounts between 10% and 20%. BSA is generally included in amounts between 0.1% and 3.0%. However, due to the unpredictability in source and quality of these proteins, it has been found that these animal proteins may include viruses and perhaps other foreign trace elements, such as hormones and pathogens, which can be an impediment to the growth and maturation of the embryos. Additionally, these elements may impede the international movement of embryos due to the various regulations countries impose upon the importation of biological substances. Thus, the use of substantial amounts of animal proteins in an embryo culture medium creates difficulty in shipping embryos across international borders.

In view of the potential problems associated with the inclusion of proteins in bovine embryo culture media, efforts have been made to find suitable non-biological substitutes for these animal proteins.

SUMMARY OF THE INVENTION

It is an object of the present invention to provide an embryo culture medium capable of extending the useful life of embryos in vitro.

It is another object of the present invention to develop a simple medium that will support bovine blastocyst development in vitro.

It is further an object of the present invention to provide a bovine embryo culture medium which utilizes non-biological substitutes in order to substantially eliminate the need for animal proteins such as fetal calf serum and substantially reduce the need for bovine serum albumin.

It is another object of the present invention to provide a bovine embryo culture medium suitable for nuclear transfer embryos.

These objects and others are met by the present invention which is directed to a bovine embryo culture medium comprising a culture solution containing the nutritional substances necessary to support a bovine embryo, wherein one of the nutritional substances consists of hemicalcium lactate in an amount effective to maintain the health and viability of the bovine embryo.

The present invention is further directed to a method for the in vitro development of bovine embryos to the blastocyst stage, comprising adding bovine embryos to a culture solution containing the nutritional substances necessary to support a bovine embryo, wherein one of the nutritional substances consists of hemicalcium lactate in an amount effective to maintain the health and viability of the bovine embryo.

The present invention is further directed to a method for the in vitro development of nuclear transfer embryos comprising adding bovine embryos to a culture solution containing the nutritional substances necessary to support a bovine embryo, wherein one of the nutritional substances consists of hemicalcium lactate in an amount effective to maintain the health and viability of the bovine embryo.

The present invention is further directed to a bovine nuclear transfer embryo culture medium comprising a culture solution containing the nutritional substances necessary to support a bovine embryo, wherein one of the nutritional substances consists of hemicalcium lactate in an amount effective to maintain the health and viability of the bovine embryo.

The present invention is further directed to a bovine nuclear transfer embryo culture medium in which bovine embryos will develop without the requirements for fetal calf serum or co-culture with other biological proteins or animal tissues, and which does not require exogenous pyruvate in the presence of L-lactate.

The present invention is further directed to bovine embryos developed by the above-referenced methods.

The advantages to the present invention are that a bovine embryo culture medium can be developed without the requirement for serum, specifically fetal calf serum, or the use of a co-culture of animal cells or other biological media, i.e., media comprising animal cells (e.g. epithelial cells) or other complex proteins. As described above, biological media have some disadvantages in that they may contain trace factors which may be harmful to the embryos and which are difficult to detect, characterize and eliminate. Thus, it would be nearly impossible to obtain identical batches of biological media. Further, the bovine embryo culture medium of the present invention requires only a minimal amount of BSA.

The bovine embryo culture media of the present invention is also advantageous in that it can allow the development of bovine embryos without the requirements of glucose and phosphates, which have been found to be toxic in culture media.

Additionally, it is believed that the bovine culture medium of the present invention is the first non-serum, non co-culture medium to allow significant in vitro production of embryos after nuclear transfer. Nuclear transfer involves the nuclear transplantation from a multi-cell embryo to a plurality of embryonic single cells. It has the potential of producing large numbers of identical animals. The nuclear transfer process involves removing the nucleus from the recipient oocyte, introducing the membrane-bounded nucleus of a donor embryo cell into the perivitelline space of the enucleated recipient oocyte, orienting the respective plasma membranes of the donor membrane-bounded nucleus and enucleated recipient oocyte, and inducing activation of the oocyte and fusion of the donor membrane-bounded nucleus into the enucleated recipient oocyte. In practice, it has been found that nuclear transfer embryos are quite sensitive and are very susceptible to disruption caused by environmental changes and stresses.

Thus, the embryo culture medium of the present invention has great application in the field of bovine embryo development, international marketing of bovine embryos, and in the in vitro production of bovine embryos after nuclear transfer.

Further objects, features and advantages of the present invention will be apparent from the following detailed description when taken in conjunction with the accompanying drawings.

DETAILED DESCRIPTION OF THE INVENTION

The bovine embryo culture medium of the present invention is specifically directed to preserving bovine embryos for a given length of time in a medium that is relatively simple to prepare and that will support bovine blastocyst development in vitro.

The requirements of an in vitro bovine embryo culture system are that it be simple to care for and use, reliable and consistent, reproducibly defined, without complex biological components such as serum, capable of supporting development to a stage compatible with nonsurgical uterine transfer, and capable of producing viable embryos with the potential of yielding normal offspring.

The embryo culture medium of the present invention advantageously comprises a simple formula. As with most culture media known to the art, the culture medium includes a culture solution containing substances which are nutritionally necessary to support the embryos. Advantageously, the simple embryo culture medium of the present invention is formed without the requirement for fetal calf serum and glucose. For purpose of the present application the term "simple bovine embryo culture medium" or "simple embryo culture medium" refers to the bovine culture medium of the present invention, which does not contain fetal calf serum, new born serum, steer serum or glucose.

Examples of the main components include hemicalcium L-lactate, sodium chloride, potassium chloride, sodium bicarbonate and a minor amount of fatty-acid free BSA. Additionally, a defined quantity of essential and non-essential amino acids may be added to the medium.

Salts are added to the medium to maintain a proper osmotic pressure or osmolarity of the medium. For the simple bovine embryo culture medium of the present invention, the preferred osmotic pressure is 265 milliosmoles (mOSM). The concentration of salt generally ranges from 0 Mm to 155 mM, preferably 110 mM to 115 mM. Examples of salts include sodium chloride and potassium chloride, preferably sodium chloride.

Potassium chloride is also added to the medium to provide a source of potassium, which is necessary in several biochemical pathways. The amount of potassium chloride ranges from 0 mM to 25 mM, preferably 1 mM to 3 mM.

Sodium bicarbonate is added to the medium to maintain a proper pH in the medium. For example, using a 5% $CO_2$ incubator with 26 mM sodium bicarbonate yields a buffered medium of approximately 7.2 pH. The amount of sodium bicarbonate ranges from 5 mM to 40 mM, preferably 24 mM to 26 mM.

The fatty-acid free BSA is added as a surfactant, i.e., to prevent the embryos from adhering to each other. Unlike culture media known to the art, the culture medium of the present invention requires only a minimal amount of the fatty-acid free BSA. For purposes of the present invention, the term "fatty-acid free bovine serum albumin" or "fatty-acid free BSA" may be used to denote various forms of fatty-acid free BSA. Examples of fatty-acid BSA include Fraction V Fatty-Acid BSA (Sigma Chemicals, St. Louis, MO.) and crystalline fatty-acid free BSA. The fatty-acid free BSA is added in amounts ranging from 1 mg/ml to 6 mg/ml, preferably 1 mg/ml to 3 mg/ml, and most preferably 3.0 mg/ml.

Of significance to the present invention is the addition of hemicalcium L-lactate in amounts ranging from 1.0 mM to 10 mM, preferably 1.0 mM to 5.0 mM. For purposes of the present invention, the terms "hemicalcium L-lactate" and "hemicalcium lactate" are used interchangeably. Hemicalcium L-lactate is L-lactate with a hemicalcium salt incorporated thereon. It is not believed that a bovine embryo culture medium has been prepared prior to this invention which incorporates hemicalcium L-lactate therein. Hemicalcium L-lactate is significant in that a single component satisfies two major requirements in the culture medium: 1) the calcium requirement necessary for compaction and cytoskeleton arrangement; and 2) the lactate requirement necessary for metabolism and electron transport. Hemicalcium L-lactate also serves as valuable mineral and energy source for the medium necessary for viability of the embryos.

A preferred embodiment of the present bovine embryo development culture medium, designated "CR1," contains the following components in the following quantities:

sodium chloride—114.7 mM
potassium chloride—3.1 mM
sodium bicarbonate—26.2 mM
hemicalcium L-lactate—5 mM
fatty-acid free BSA—3 mg/ml It is also within the scope of the present invention to add antibiotically effective amounts of an agent, such as gentamicin sulfate, penicillin, streptomycin, fungizone or other antibiotics known to the art. Additionally, a cryopreservation agent, known to the art, may be added to protect the cellular integrity of the bovine embryo during freezing operations. Further, chemical buffers, such as HEPES, may by added to maintain the proper pH in the absence of $CO_2$.

The bovine culture medium of the present invention does not appear to benefit from added pyruvate or vitamins, but is improved when amino acids are added. Although Kane, M. T. and B. D. Bavister (1988, "Vitamin Requirements for Development of Eight-Cell Hamster Embryos to Hatching Blastocysts In Vitro," *Biol Reprod.*, 39, 1137–1143) had earlier demonstrated that vitamins were beneficial for development of hamster embryos, this did not appear to be the case in the present invention. However, it is noted that Kane and Bavister used different vitamins than those demonstrated in Experiment 5 (supra.). Zhang X. and D. T. Armstrong (1990, "Presence of Amino Acids and Insulin in a Chemically Defined Medium Improves Development of 8-Cell Rat Embryos In Vitro and Subsequent Implantation In Vivo, *Biol. Reprod.*, 42, 662–668) demonstrated an increased effect of amino acids on rat embryo development in vitro and that the inclusion of amino acids with insulin gives superior development in vitro as well as improved pregnancy rates after transfer to recipients.

The embryo culture medium of the present invention may either be used simply as a collection material to hold the embryo after it has been flushed from the donor animal or after nuclear transfer has taken place, or it may be used for storing or developing the embryos for an extended period of time. If the bovine culture medium of the present invention is used for cryopreservation of bovine embryos, then a cryopreservation agent, such as glycerol or dimethyl sulfoxide may be added.

Embryo development may also be enhanced by addition of components believed to be beneficial, such as steroids including estrogens, progestins, corticosteroids, and androgens, estrogen growth factor, transforming growth factor, epidermal growth factor, fibroblast growth factor, differentiating (lymphocyte) growth factor, insulin, insulin-like growth factor, transferrin, selenium, fatty acids and their derivatives such as prostaglandins and leukotrienes, inositol, and other phospholipids.

The present invention will now be described with respect to the following examples, which are not intended to limit the scope of the invention in any way.

EXAMPLES

The common procedures for Experiments 1–5 were as follows:

Two ml of a maturation media were prepared according to the procedure of Sirard et al. (1988, *Biol. Reprod.*, 39, 546–552), which is incorporated herein by reference, by combining 1.8 ml TCM 199, 0.2 ml heat-treated fetal calf serum (60° C. for 30 min), 10% final, 20 $\mu$l pyruvate stock (0.2 mM final), 10 $\mu$g NIH oLH (0.0230 Units, Lot oLH #24, 5 $\mu$g/ml final), 1 $\mu$g NIH oFSH (0.2 units, Lot oFSH #15), .5 $\mu$g/ml final, and 1 $\mu$l gentamicin stock (50 mg/ml, 25 $\mu$g/ml final). The medium was filter-sterilized using 0.22 $\mu$m pore size filters, and 2 $\mu$l estrogen (1 $\mu$g/ml final from a stock of 1 mg/ml) was added.

The oocyte-cumulus complexes (OCC) were aspirated from ovaries recovered from a slaughterhouse in Milwaukee, WI. The ovaries were transported from the slaughterhouse to the laboratory in insulated containers with saline (0.9%; 30°±2° C.). After arrival, the ovaries were washed with 30° C. water and placed into a flask containing fresh saline (0.9%) in a water bath maintained at 30° C. Follicular contents were harvested using an 18-gauge needle and accumulated in a 50 ml sterile conical tube (Falcon #2070). Following aspiration, OCC were located using 100 mm plates in a warm room (30°±2° C.) using a stereomicroscope. The OCC were washed 4 times through low bicarbonate-TALP (Parrish, J. J. et al., (1988, "Capacitation of Bovine Sperm by Heparin," *Biol. Reprod.* 38, 1171–1180, incorporated herein by reference) and placed into maturation plates (10 OCC per 50 ul drop). Maturation plates consist of ten 50 ul drops of maturation medium with estradiol-17B (1 ug/ml), FSH (0.5 ug/ml) and LH (0.5 ug/ml) (Sirard et al., supra., 1988) in a 60 mm petri dish with 10 ml of paraffin oil.

Fertilization of oocytes was performed according to the procedure described in Sirard et al. (supra., 1988). Briefly, OCC were in vitro matured 22±2 hours, then washed 2 times through Sp-TALP (Parrish, J. J. et al, supra. 1988) and moved into fertilization plates. Fertilization was performed in 60 mm plates with 10 drops (40 $\mu$l each) of fertilization medium (5 ml TL Stock-no glucose, 30 mg fatty-free BSA-6 mg/ml final, 50 $\mu$l pyruvate stock-0.2 mM final, 2.5 $\mu$l gentamicin-25 $\mu$g/ml final-optional) optional) covered with oil and 10 OCC for each drop. The OCC were added, followed by $5 \times 10^4$ motile sperm, 0.2 ug of heparin, and 2 ul of PHE stock (20 $\mu$m penicillamine, 10 $\mu$m hypotaurine, 1 $\mu$m epinephrine, 21 $\mu$m sodium metabisulfate, and 118 $\mu$m DL-lactate syrup in 9% sodium chloride according to Leibfried, M. L. and B. D. Bavister, 1982, "Effect of Epinephrine and Hypotaurine on in vitro Fertilization in the Golden Hamster," *J. Reprod. Fertil.*, 66, 87–93).

Motile sperm cells were prepared by the Percoll separation of frozen sperm procedure. A 45% percoll solution (3.090 ml/100 ml KCl, 2.920 ml/100 ml $NaH_2PO_4$, 4.675 g/100 ml NaCl, 2.380 g/100 ml HEPES, adjust the pH to 7.3) was prepared by a 1:1 dilution with 90% percoll using Sperm TL Stock Solution (SPTL) (2.10 mM $CaCl_2 2H_2O$, 3.1 mM KCl, 0.4 mM $MgCl_2 6H_2O$, 100 mM NaCl, 0.29 mM $NaH_2PO_4 H_2O$, 21.6 mM Lactic Acid, 10 mM Hepes, 25 mM $NaHCO_3$, adjust pH to 7.4 before bringing to final volume; check osmolarity: 290–300 mOSM) according to Parrish, J. J. et al., supra. 1988. The SPTL did not contain BSA. Two—three ml of 90% percoll was placed on the bottom of a conical tube (Falcon 2095). Two ml of 45% percoll was layered carefully on the top of the 90% percoll. The procedure was performed at room temperature. One unit of semen was thawed (35° C., 1 min.) and layered on top of the percoll gradients. The tube was centrifuged at 700×g for 30 min. The top layers were removed, and the concentrated motile sperm was available for use.

Following 44±2 hours after insemination, the OCC were stripped of cumulus cells, and the eggs were categorized as cleaved ($\leq$2 cells) or uncleaved. The cleaved eggs were randomly assigned to treatment with approximately 20 embryos per bovine embryo culture medium development drop (50 ul).

In Experiments 1–4, the embryos were left in the bovine embryo culture development medium for 5 days.

In the amino acid experiment (Experiment 5), the maturation was the same but fertilization was in the same type of medium as their subsequent development medium and the OCC were not stripped until 68±2 hours after insemination. The embryos remained in development medium for 3 days after cumulus removal.

In all experiments the number of morulae and blastocysts were determined on day 7 with the day of maturation representing day 0. The results are presented as percentage of cleaved embryos developed to the morula or blastocyst stage.

Statistical analyses were conducted using SAS (1982). Analysis of variance was conducted with the appropriate main effects and replicates included in the model. The results are expressed as the percentage of cleaved embryos that attained the morula or blastocyst stage. Means were considered different if the main effect was significant ($P<0.05$) and the PDIF function was significant ($P<0.05$).

EXPERIMENT 1

Experiment 1 was designed to test the effect of hemi-calcium L-lactate and sodium pyruvate on bovine embryos in the culture medium. Experiment 1 was a 2×3 factorial treatment structure with 5 versus 10 mM hemicalcium L-lactate and 0.2, 0.4, and 5 mM sodium pyruvate.

Figure 1:
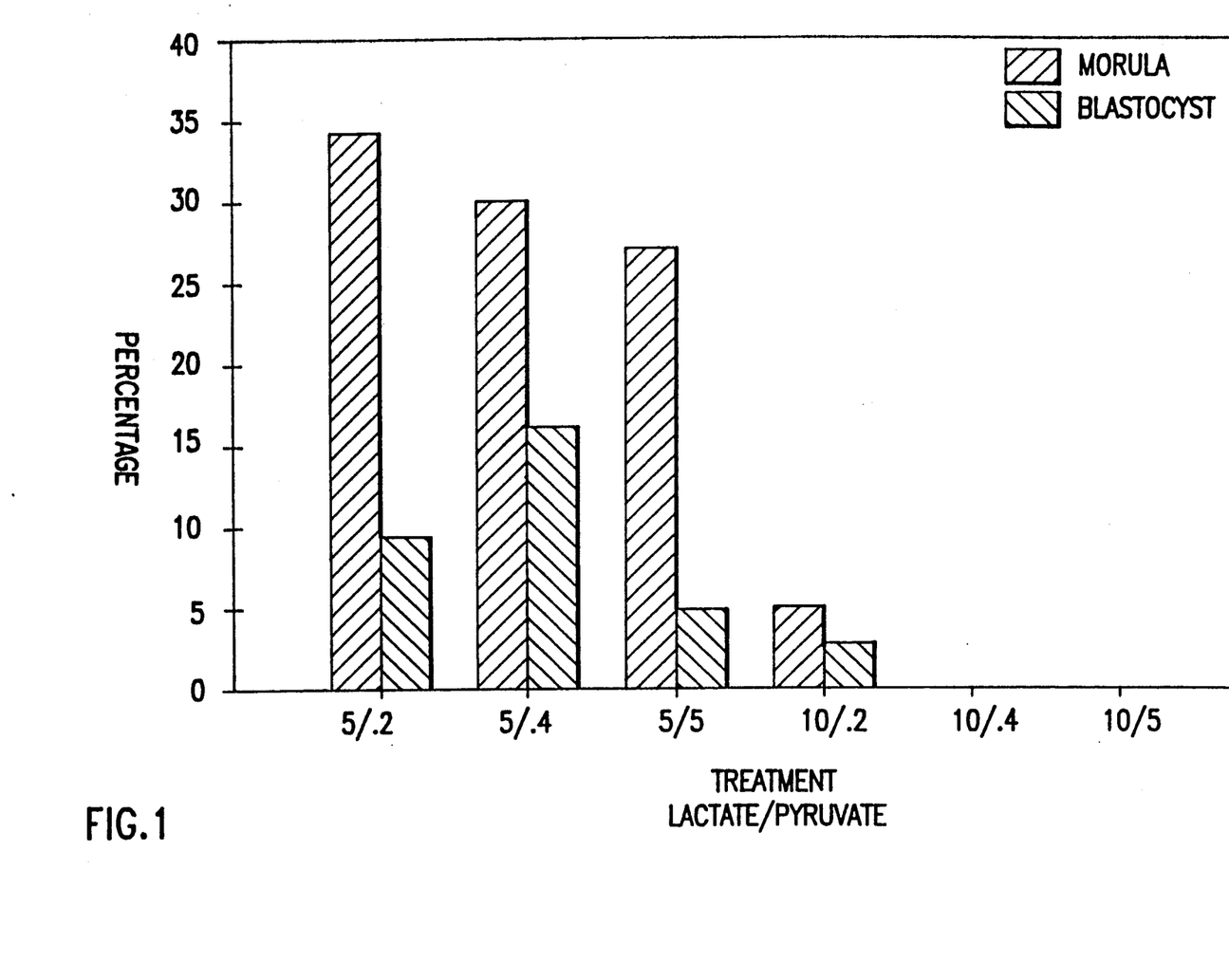
FIG. 1 is a graph illustrating the effects of hemicalcium L-lactate and sodium pyruvate in the bovine culture medium of the present invention on the morula and blastocyst formation of bovine embryos.

This experiment was replicated 4 times with a total of 886 oocytes, with an average cleavage rate of 65.7% yielding 582 embryos. As illustrated in FIG. 1, there was a dramatic difference between 5 and 10 mM hemicalcium L-lactate. The 5 mM concentration yielded significant development, whereas the 10 mM did not. Pyruvate dosage did not effect (P>0.05) the percentage of embryos reaching the morula or blastocyst stage. However, morula and blastocyst development was decreased (P<0.001) by the addition of an extra 5 mM hemicalcium L-lactate to CR1 (total of 10 mM L-lactate and 5 mM calcium).

Based upon this experiment, it was determined that bovine embryo development was capable in the following simple, serum-free culture medium: 114.7 mM sodium chloride, 3.1 mM potassium chloride, 26.2 mM sodium bicarbonate, 5 mM hemicalcium lactate, 0.3% fatty-acid free bovine serum albumin, and gentamicin sulfate as an antibacterial agent. This medium is designated CR1.

EXPERIMENT 2

Experiment 2 was designed to compare the effects of added magnesium sulfate ($MgSO_4$) (0.5 mM) and tetrasodium ethylenediaminetetraacetic acid (EDTA) (10 $\mu$M) on bovine embryos in the culture medium. Magnesium sulfate and EDTA were evaluated in a 2×2 factorial treatment structure.

A total of 715 oocytes from 6 replicates were started for this experiment with an average cleavage rate of 65.5% resulting in 468 usable embryos. Neither morula nor blastocyst percentage was significantly affected by the addition of $MgSO_4$ or EDTA. However, when the percentage of morula and blastocyst were combined, the addition of 0.5 mM $MgSO_4$ tended (P=0.12) to decrease development (43.2±3.8 versus 37.1±2.2 in the presence of $MgSO_4$).

Figure 2:
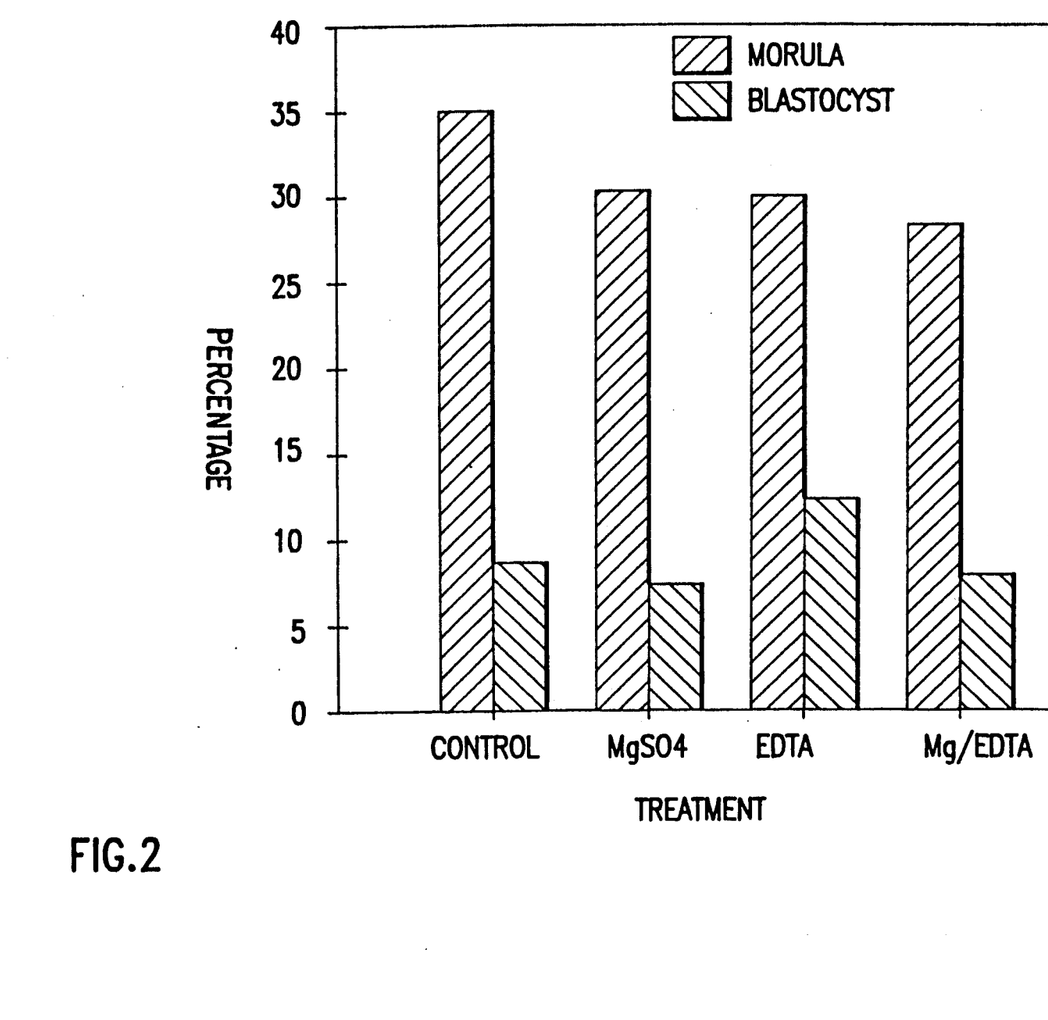
FIG. 2 is a graph illustrating the effects of magnesium sulfate and tetrasodium-EDTA in the bovine culture medium of the present invention on the morula and blastocyst formation of bovine embryos.

As illustrated in FIG. 2, neither magnesium sulfate nor EDTA had an effect on development.

EXPERIMENT 3

Experiment 3 was designed to test the effect of added calcium and lactate to the bovine culture medium determined in Experiment 1 to provide the best results with respect to hemi-calcium lactate concentration, i.e., the 5 mM hemicalcium L-lactate culture medium. Experiment 3 was further designed to determine whether it was the increased calcium, lactate, or their combination that decreased development at 10 mM hemicalcium L-lactate. Control medium was CR1 with 0.2 mM sodium pyruvate. Treatment structure was a 2×2 factorial with 0 or 2.5 mM added calcium chloride and 0 or 5 mM added free L-lactic acid.

Four replicates with a total of 946 oocytes were used for this experiment. The average cleavage rate was 58.8% resulting in 556 embryos used for experimentation. Morula percentage was decreased (P<0.05) by the interaction of added calcium and L-lactate. On the other hand, blastocyst development was not affected by either the main effects or their interaction.

Figure 3:
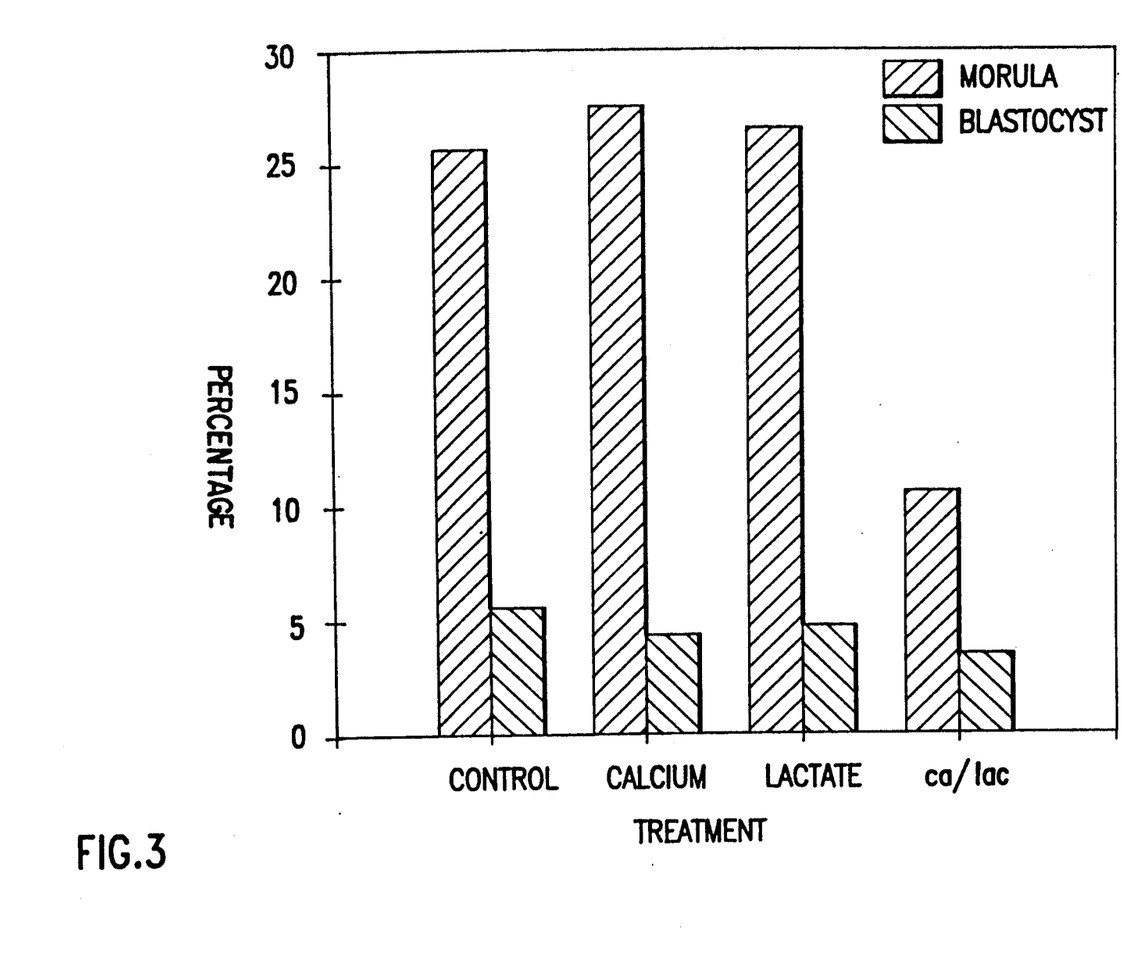
FIG. 3 is a graph illustrating the effects of the interaction of calcium and lactate in the bovine culture medium of the present invention on the morula and blastocyst formation of bovine embryos.

As illustrated in FIG. 3, it was determined that the combination of high levels of calcium and lactate was detrimental to bovine embryo development.

EXPERIMENT 4

Experiment 4 was designed to test whether exogenous pyruvate was necessary for bovine embryo development in the presence of 5 mM hemicalcium L-lactate. Four doses of sodium pyruvate (0, 0.2, 0.4 and 5 mM) were examined. The linear effect of pyruvate was determined using the following coefficients: $-1.4, -1.2, -1$ and 3.6, respectively, for 0, 0.2, 0.4 and 5 mM.

Figure 4:
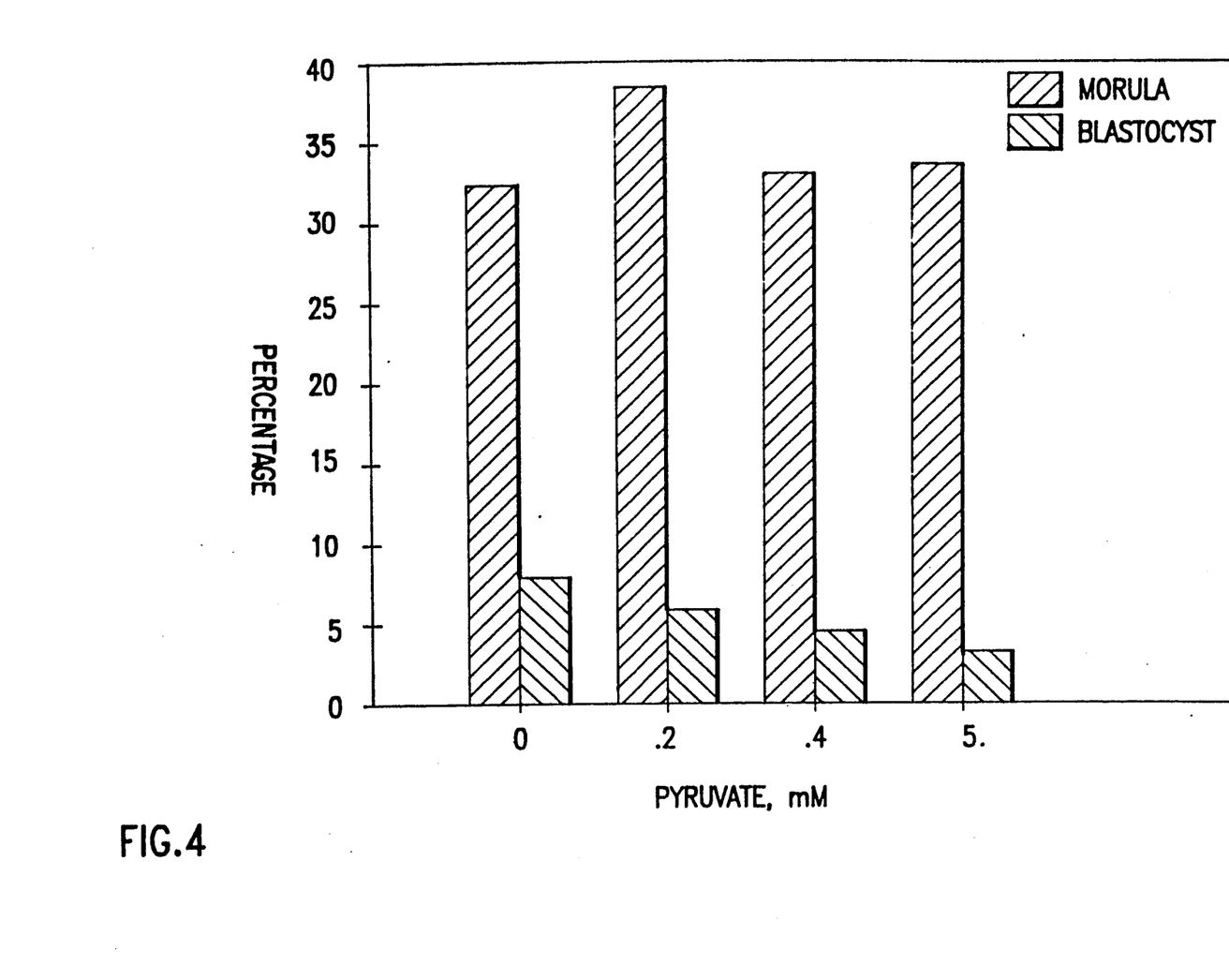
FIG. 4 is a graph illustrating the effects of the exogenous pyruvate in the presence of 5 mM hemicalcium L-lactate in the bovine culture medium of the present invention on the morula and blastocyst formation of bovine embryos.

Four replicates utilizing 425 oocytes with an average cleavage rate of 68.2% yielded 290 embryos for use in this experiment. In the presence of 5 mM hemicalcium L-lactate, pyruvate had no effect (P>0.34) on embryo development when added in the 0 to 5 mM range. The linear contrast also was not significant. As illustrated in FIG. 4, it was determined that exogenous pyruvate is not necessary for the development of bovine embryos in a culture medium containing hemicalcium L-lactate.

EXPERIMENT 5

Experiment 5 was designed to determine the effects of essential (BME) amino acids with 1 mM L-glutamine (EAA), MEM non-essential amino acids (NEA), and MEM vitamins (VIT) on the development of bovine embryos in the embryo culture medium CR1 of Experiment 1. The five treatment (TRT) groups were as follows:

1: Control (CR1) (5 mM hemicalcium L-lactate)+0.4 mM pyruvate and 1 mg/100 ml phenol red
2: Control+EAA*+NEA+VIT*
3: Control+EAA+NEA
4: Control+EAA+VIT
5: Control+NEA+VIT

| Component | Quantity (g/L) |
|---|---|
| EAA*: BME Essential Amino Acids (Sigma) having the following components: | |
| L-Arginine-HCl | 1.050 |
| L-Cystine | 0.600 |
| L-Histidine | 0.400 |
| L-Isoleucine | 1.300 |
| L-Leucine | 1.300 |
| L-Lysine-HCl | 1.849 |
| L-Methionine | 0.375 |
| L-Phenylalanine | 0.825 |
| L-Threonine | 1.200 |
| L-Tryptophan | 0.200 |
| L-Tyrosine | 0.900 |
| L-Valine | 1.175 |
| L-Glutamine | 7.300 |
| NEA**: MEM Non-Essential Amino Acids (Sigma) having the following components: | |
| L-Alanine-HCl | 0.890 |
| L-Asparagine (monohydrate) | 1.500 |
| L-Aspartic Acid | 1.330 |
| L-Glutamic Acid | 1.470 |
| Glycine | 0.750 |
| L-Proline | 1.150 |
| L-Serine | 1.050 |
| VIT***: Vitamin solution (Sigma) having the following components: | |
| Choline Chloride | 0.100 |
| Folic Acid | 0.100 |
| Myo-Inositol | 0.200 |
| Niacinamide | 0.100 |
| α-Pantothenate (calcium) | 0.100 |
| Pyridoxal-HCl | 0.100 |
| Riboflavin | 0.010 |
| Sodium Chloride | 8.500 |
| Thiamine-HCl | 0.100 |

In this experiment, treatments were imposed at fertilization rather than after insemination. The experiment was conducted as a 2×5 factorial, including two cumulus groups. The cumulus cells were stripped at the end of maturation (removed) or at 68±2 hours post-insemination (intact). The effects of the amino acids and vitamins on bovine embryo development are illustrated in the following table:

| TRT | CO[a] | # EMBRYOS | # EMBRYOS CLEAVED | % CLEAVED MORULA | % CLEAVED BLASTOCYST[b] |
|---|---|---|---|---|---|
| 1 | + | 326 | 217 | 31.4 ± 4.0 | 10.2 ± 3.1[d, e] |
| 1 | − | 292 | 135 | 41.2 ± 4.0 | 5.1 ± 3.1[e] |
| 2 | + | 329 | 231 | 26.3 ± 4.0 | 21.0 ± 3.1[c] |
| 2 | − | 271 | 134 | 22.5 ± 4.0 | 24.4 ± 3.1[c] |
| 3 | + | 352 | 243 | 25.5 ± 4.0 | 21.4 ± 3.1[c] |
| 3 | − | 317 | 165 | 18.5 ± 4.0 | 28.6 ± 3.1[c] |
| 4 | + | 351 | 246 | 20.9 ± 4.0 | 10.5 ± 3.1[d, e] |
| 4 | − | 314 | 179 | 20.0 ± 4.0 | 14.5 ± 3.1[d] |
| 5 | + | 334 | 219 | 23.7 ± 4.0 | 5.3 ± 3.1[e] |
| 5 | − | 338 | 167 | 18.9 ± 4.0 | 14.6 ± 3.1[d] |

[a]CO+ means cumulus stripped at about 65 hours post insemination
CO− means cumulus removed prior to insemination
[b]least squares means of 5 replicates with main effects of replicate and treatment
[c, d, e]means without common superscripts are different (P < 0.05)

Figure 5:
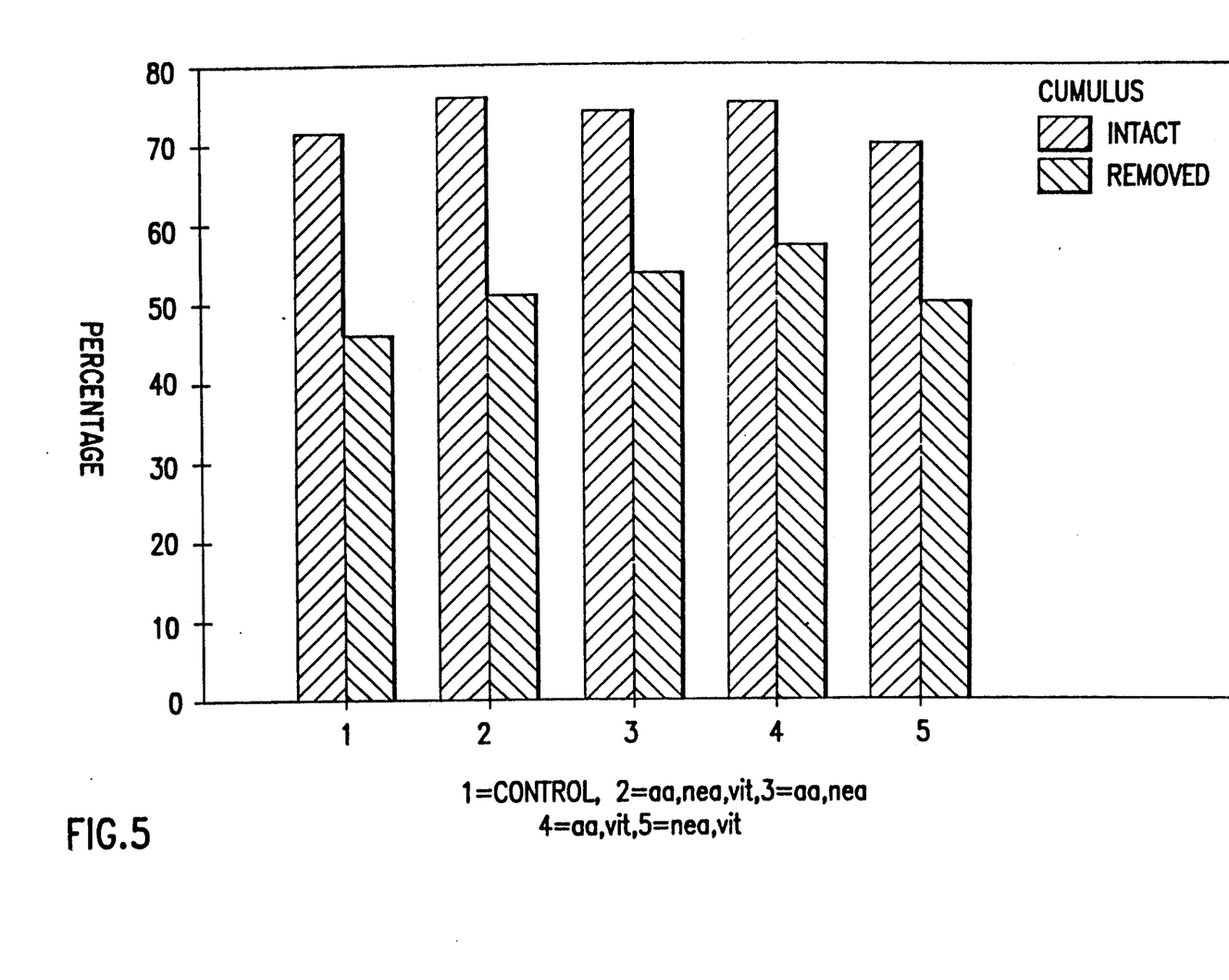
FIG. 5 is a graph illustrating the effects of varying treatments involving BME amino acids with 1 mM L-glutamine (AA), MEM non-essential amino acids (NEA), and/or MEM vitamins (VIT) in the bovine culture medium of the present invention on the cleavage rate of bovine embryos.

As illustrated in FIG. 5, there did not appear to be any overall effect of any of the treatments on the rate of cleavage.

Figure 6:
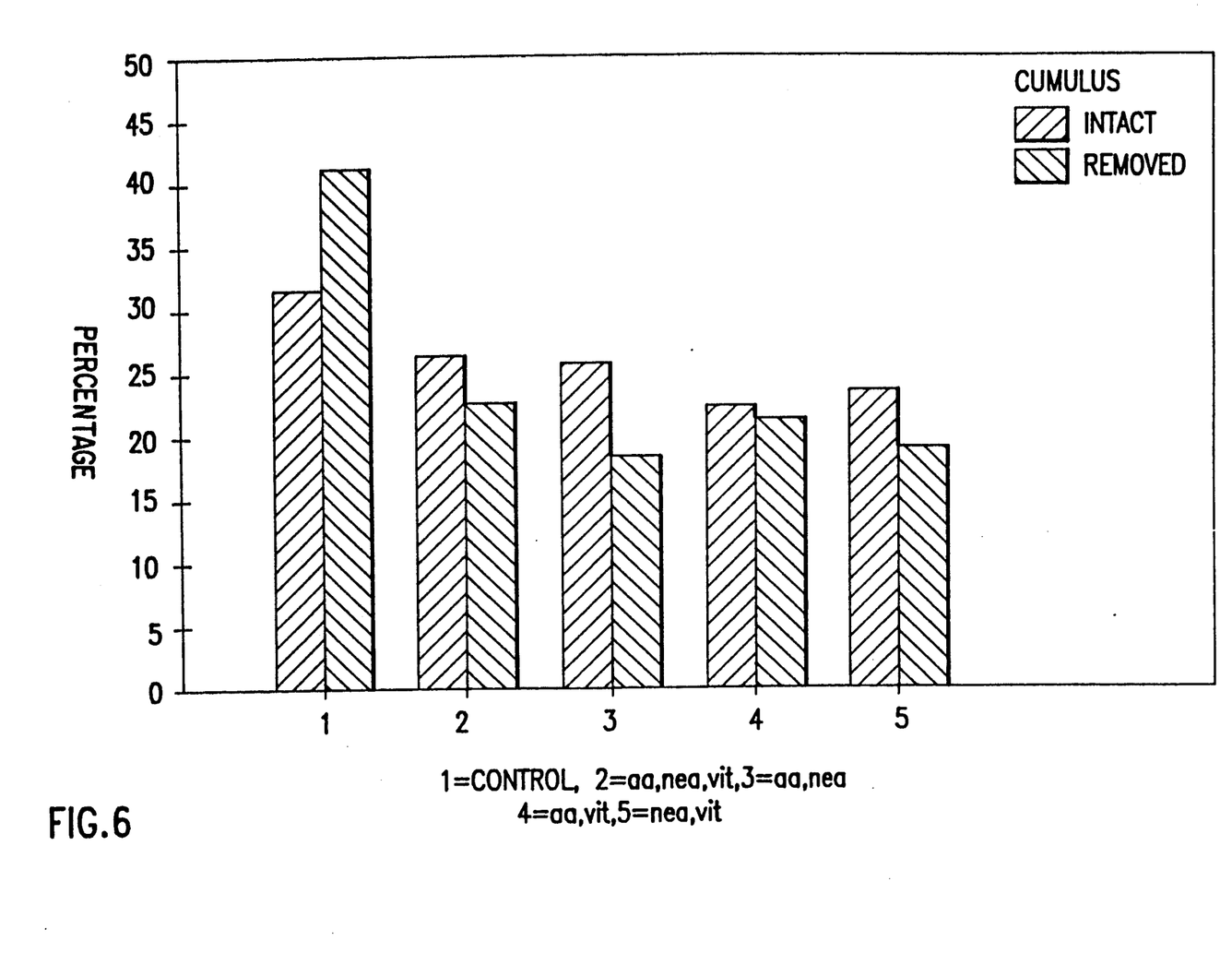
FIG. 6 is a graph illustrating the effects of varying treatments involving BME amino acids with 1 mM L-glutamine (AA), MEM non-essential amino acids (NEA), and/or MEM vitamins (VIT) in the bovine culture medium of the present invention on the morula formation of bovine embryos.
Figure 7:
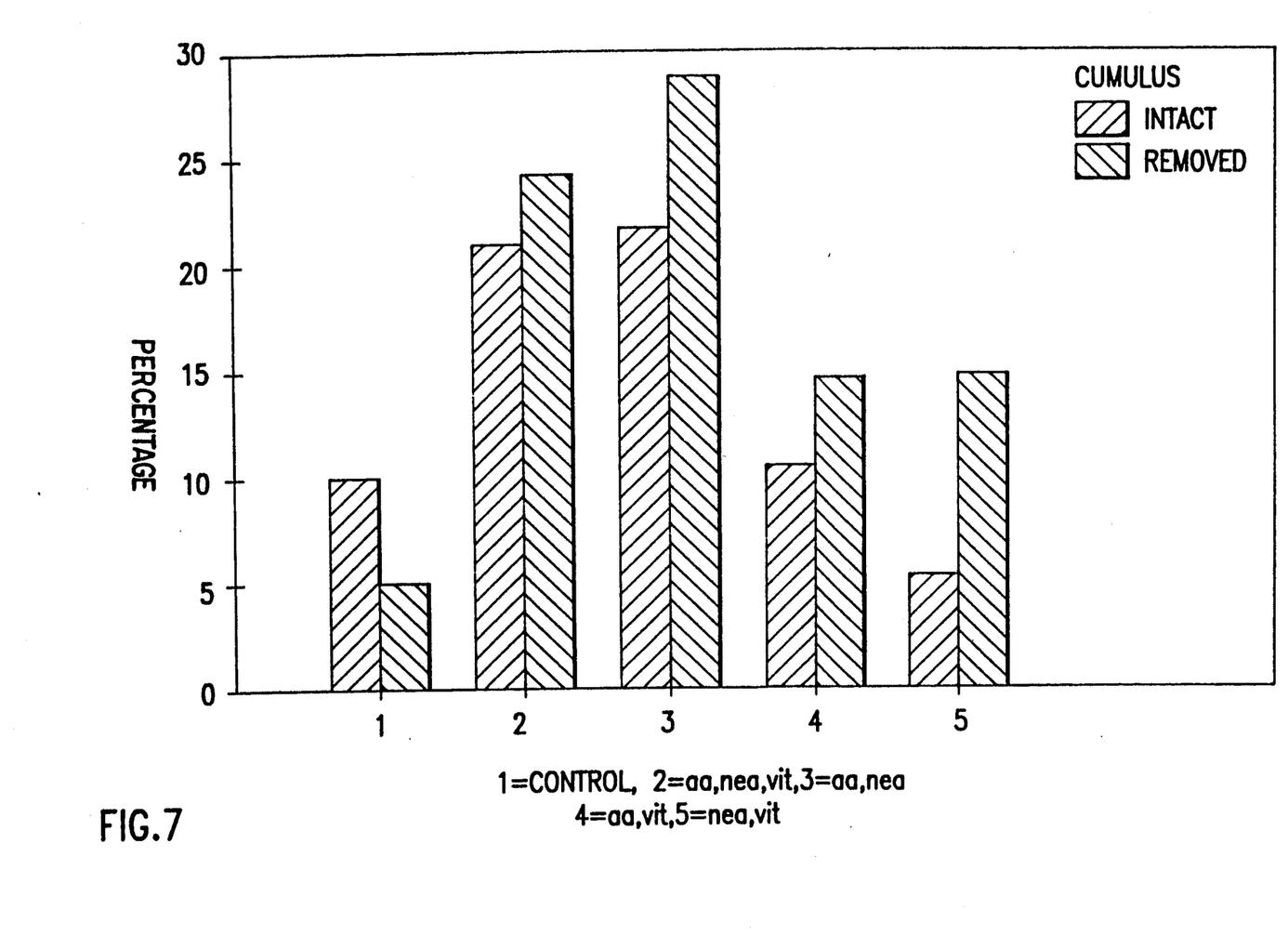
FIG. 7 is a graph illustrating the effects of varying treatments involving BME amino acids with 1 mM L-glutamine (AA), MEM non-essential amino acids (NEA), and/or MEM vitamins (VIT) in the bovine culture medium of the present invention on the blastocyst formation of bovine embryos.

As illustrated in FIG. 6, morula formation was decreased by the addition of AA, NEA and VIT presumably because the morula advanced to blastocysts as illustrated in FIG. 7.

As illustrated in FIG. 7, both AA and NEA increased the blastocyst percentage, but VIT appeared to have a detrimental effect.

EXPERIMENT 6

Experiment 6 was designed to compare the bovine culture medium CR1 of the present invention with a known culture medium Hamster Embryo Culture Medium-2 (HECM-2) (Seshagiri, P. B. and B. D. Bavister, 1989, "Glucose Inhibits Development of Hamster 8-cell Embryos In Vitro," Biol. Reprod., 40, 599–606) in terms of use in nuclear transfer bovine embryos (NTs). HECM-2 was glucose free, sodium dihydrogen phosphate free and contained 4 amino acids (0.1 mM phenylalanine, 0.2 mM isoleucine, 0.05 mM methionine and 1 mM glutamine) and 0.1 mM pyruvate. Oviductal oocytes obtained by salpingectomy from superovulated heifers were used as the recipient cytoplasm for both fresh and frozen donor embryos. Metaphase chromosomes were removed from each oocyte (enucleation), a cell from the donor embryo transferred into the perivitelline space of the oocyte, and the two cells (recipient cytoplasm and embryonic cell) were induced to fuse by an electrical pulse (see Prather, R. S. et al., 1987, Nuclear Transfer in the Bovine Embryo: Assessment of the Donor Nuclei and Recipient Cytoplasm," Biol. Reprod., 37, 859–866). After fusion, the NTs were placed into 30 μl drops of HECM-2 supplemented with 20% heat-inactivated cow serum or CR1 under a paraffin oil overlay and incubated at 39° C. in 5% $CO_2$. Embryo development was observed over a period of approximately a week. As illustrated in the following table, approximately 13% of those cultured in vitro in CR1 developed to the morula or blastocyst stage of which half were classified as usable and either transferred, stored frozen, or used in recloning, versus approximately 11% of those cultured in HECM.

| Development of Nuclear Transfer Bovine Embryos Cultured In Vitro | | | |
|---|---|---|---|
| Culture Media[a] | Number Cultured | Number Morula (%) | Number Blastocyst (%) |
| CR1 | 171 | 10 (10.0%) | 5 (2.9%) |
| HECM | 174 | 16 (9.2%) | 3 (1.7%) |

[a]CR1 contains fatty-acid free BSA; HECM contains 20% cow serum

EXPERIMENT 7

Experiment 7 was designed to determine if NTs could be developed in vitro in the bovine embryo culture medium of the present invention. Nuclear transfer embryos were produced according to Prather et al., 1987, Biol. Reprod., 37,859–866, which is incorporated herein by reference. Specifically, in vitro matured oocytes were used as recipients, in vitro developed embryos were used as donors, and the subsequently formed NTs were developed in vitro in CR1 with 1 mM L-glutamine (CR1-L-GLN).

The Treatment structure was a blocked one-way design with 3 treatments. Each donor embryo served as the block, i.e., every treatment was imposed on NTs from each donor. Enucleation and transfer of donor blastomeres was performed at 24 hours post-oocyte maturation. The three treatments were as follows: 1) fusion of the NTs at 30 hours; 2) those NTs that did not fuse at 30 hours and were then refused at 42 hours; and 3) fusion at 42 hours. The NTs were maintained in CR1-L-GLN during the waiting period before fusion as well the development period. The results are illustrated in the following table:

| | Nuclear Transfer - Fusion at 30 Hours Versus 24 Hours | | |
|---|---|---|---|
| FUSION[a] | ACTIVATION | CLEAVAGE[a] | DEVELOPMENT MORULA + BLASTOCYST[b, c] |
| 30 hr | | | |
| N 68/127 | 68/97 | 21/68 | 2/5 |
| % 54 | 71 | 31 | 3.4 |
| 30/42 hr | | | |
| N 38/51 | . | 23/38 | 7/32 |
| % 75 | | 61 | 22 |
| 42 hr | | | |
| N 107/132 | 80.99 | 76/109 | 28/87 |
| % 81 | 81 | 71 | 32 |

[a]11 donor embryos
[b]9 donor embryos
[c]cultured 5 days in CR1 + glutamine (1 mM)

The results indicate that NTs will develop in CR1 from in vitro matured oocytes at approximately the same rate as in the sheep (see Prather et al., supra., 1987). Further, when the fusion regime is changed to a later time period development of NTs is similar to that of normal in vitro matured fertilized and developed oocytes.

It is understood that the invention is not confined to the particular construction and arrangement herein described, but embraces such modified forms thereof as come within the scope of the following claims.

We claim:

1. A bovine embryo culture medium comprising a culture solution containing the nutritional substances necessary to support a bovine embryo, wherein one of said nutritional substances is hemicalcium lactate in an amount effective to maintain the health and viability of the bovine embryo.

2. The bovine embryo culture medium of claim 1, wherein the remaining nutritional substances are salts, sodium bicarbonate, and fatty acid free bovine serum albumin, the remaining nutritional substances being in amounts effective to maintain the health and viability of the bovine embryo.

3. The bovine embryo culture medium of claim 2, wherein the salts are sodium chloride and potassium chloride.

4. The bovine embryo culture medium of claim 3, in which the salts are present in concentrations of approximately 0 mM to 155 mM sodium chloride and approximately 0 mM to 25 mM potassium chloride.

5. The bovine embryo culture medium of claim 2, wherein the sodium bicarbonate is present in a concentration of approximately 5 mM to 40 mM.

6. The bovine embryo culture medium of claim 2, wherein the fatty-acid free BSA is present in a concentration of approximately 1 mg/ml to 6 mg/ml.

7. The bovine embryo culture medium of claim 1, wherein the hemicalcium lactate is present in a concentration of approximately 1 mM to 10 mM.

8. The bovine embryo culture medium of claim 1, which further contains a cryopreservation agent.

9. The bovine embryo culture medium of claim 2, which further contains amino acids in amounts effective to maintain the health, viability and development of the bovine embryo.

10. The bovine embryo culture medium of claim 1, which is glucose free.

11. The bovine embryo culture medium of claim 1, which is serum free.

12. The bovine embryo culture medium of claim 1, wherein the culture solution comprises antibiotically effective amounts of penicillin, streptomycin, gentamicin sulfate or fungizone.

* * * * *